(12) United States Patent
Friedrich

(10) Patent No.: US 10,908,097 B2
(45) Date of Patent: Feb. 2, 2021

(54) METHOD FOR DETERMINING THE CONCENTRATION OF AN INGREDIENT IN A BODY OF CERAMIC OR GLASSY MATERIAL

(71) Applicant: Heraeus Quarzglas GmbH & Co. KG, Hanau (DE)

(72) Inventor: Helmut Friedrich, Dieburg (DE)

(73) Assignee: Heraeus Quarzglas GmbH & Co. KG, Hanau (DE)

(*) Notice: Subject to any disclaimer, the term of this patent is extended or adjusted under 35 U.S.C. 154(b) by 293 days.

(21) Appl. No.: 16/202,206

(22) Filed: Nov. 28, 2018

(65) Prior Publication Data
US 2019/0162678 A1    May 30, 2019

(30) Foreign Application Priority Data

Nov. 29, 2017  (EP) .................................. 17204532
Dec. 19, 2017  (EP) .................................. 17208482

(51) Int. Cl.
*G01N 22/00*  (2006.01)
*G01N 33/38*  (2006.01)
*G01S 13/88*  (2006.01)

(52) U.S. Cl.
CPC .......... *G01N 22/00* (2013.01); *G01N 33/386* (2013.01); *G01N 33/388* (2013.01); *G01S 13/88* (2013.01); *G01S 13/887* (2013.01)

(58) Field of Classification Search
CPC ..... G01N 2021/845; G01N 2021/8472; G01N 22/00; G01N 23/02; G01N 23/10;
(Continued)

(56) References Cited

U.S. PATENT DOCUMENTS 4,891,573 A * 1/1990 Kent .................. G01R 27/2664
324/629
5,455,516 A * 10/1995 Jean ....................... G01N 22/04
324/639
(Continued)

OTHER PUBLICATIONS

"Reflection and transmission properties of common construction materials at 2.4GHz frequency", Koppel, Tarmo et al. International Science Conference "Environmental and Climate Technologies", CONECT 2016, Oct. 12-14, 2016, Riga, Latvia, pp. 159-165 (Year: 2016).*

(Continued)

*Primary Examiner* — Peter M Bythrow
(74) *Attorney, Agent, or Firm* — Dicke, Billig & Czaja, PLLC

(57) ABSTRACT

Measurement methods are known for determining the concentration of an ingredient in a body of ceramic or glassy material, in which the optical path length or the signal propagation time of a measurement wave penetrating the body of ceramic or glassy material in a measurement direction is determined and evaluated. Starting therefrom, in order to indicate a non-destructive method for determining a concentration of an ingredient in a body of ceramic or glassy material, which is also suitable for measurement in the production process of the body concerned, it is suggested according to one embodiment that modulated gigahertz radiation is used as the measurement wave.

15 Claims, 3 Drawing Sheets

(58) Field of Classification Search
CPC .... G01N 23/20; G01N 33/386; G01N 33/388; G01S 13/88; G01S 13/887; G01S 13/888
See application file for complete search history.

(56) References Cited

U.S. PATENT DOCUMENTS

| | | | | |
|---|---|---|---|---|
| 6,147,503 A * | 11/2000 | Nelson | ............... | G01N 22/04 324/637 |
| 8,701,483 B2 * | 4/2014 | Welle | ............... | G01F 23/284 73/290 V |
| 9,046,404 B2 * | 6/2015 | Welle | ............... | G01F 23/284 |
| 10,184,820 B2 * | 1/2019 | Edvardsson | ......... | G01F 23/284 |
| 10,288,468 B2 * | 5/2019 | Littleford | ............... | G01S 13/34 |
| 2002/0177961 A1 * | 11/2002 | Lovegren | ............... | G01N 22/00 702/50 |
| 2004/0065831 A1 * | 4/2004 | Federici | ............ | G01N 21/3581 250/341.1 |
| 2005/0093555 A1 * | 5/2005 | Ehata | ............... | H01P 7/06 324/672 |
| 2006/0237650 A1 * | 10/2006 | Taday | ............... | G01N 21/3586 250/339.11 |
| 2009/0052764 A1 * | 2/2009 | Merkel | ............... | G01N 29/11 382/141 |
| 2009/0128395 A1 * | 5/2009 | Baath | ............... | G01S 13/88 342/124 |
| 2010/0295718 A1 * | 11/2010 | Mohamadi | ............ | G01S 13/888 342/21 |
| 2012/0256777 A1 * | 10/2012 | Smith | ............... | G01S 13/89 342/22 |
| 2015/0185143 A1 * | 7/2015 | Manneschi | ............ | G01N 33/18 250/339.12 |
| 2017/0031006 A1 | 2/2017 | Conrad | | |
| 2017/0108452 A1 * | 4/2017 | Carlson | ............... | G01S 13/751 |
| 2017/0261444 A1 * | 9/2017 | Krapf | ............... | G01N 24/082 |
| 2018/0038981 A1 * | 2/2018 | Mrvaljevic | ............ | G01S 13/888 |
| 2018/0172820 A1 * | 6/2018 | Rhead | ............... | G01S 13/888 |
| 2018/0306632 A1 * | 10/2018 | Khodjet-Kesba | ....... | G01S 13/10 |

OTHER PUBLICATIONS

"Acoustic Properties of Silica Glass Doped with Fluorine", Ting-Cun Wei, Department of Electrical Engineering, Journal of Non-Crystalline Solids 321 (2003).

* cited by examiner

METHOD FOR DETERMINING THE CONCENTRATION OF AN INGREDIENT IN A BODY OF CERAMIC OR GLASSY MATERIAL

CROSS-REFERENCE TO RELATED APPLICATION

This Utility patent application claims priority to Application No. EP 17 204 532.0, filed on Nov. 29, 2017, and Application No. EP 17 208 482.4 filed on Dec. 19, 2017 which are incorporated herein by reference.

BACKGROUND

One embodiment relates to a method for determining the concentration of an ingredient in a body of ceramic or glassy material, including the measurement of the optical path length or the signal propagation time of a measurement wave penetrating the body of ceramic or glassy material in a measurement direction.

The chemical nature of the body made of ceramic or glassy material depends on its intended use. For example, it consists partly or completely of glass, for example, quartz glass. Quartz glass here is understood to mean doped or undoped silica glass with a $SiO_2$ content of at least 85%. The glass is porous, transparent, opaque, colored, for example, it can also be black. Or the body consists partly or completely of a ceramic, for example, of a one-component ceramic such as AlN, BN, $Si_3N_4$ or SiC.

The geometric shape of the body made of ceramic or glassy material also depends on the intended use. It is used, for example, as a component or semi-finished product for the manufacture of optical fibers, in lamp production, in chemical apparatus engineering or in semiconductor production, and it is available, for example, in the form of tubes, solid cylinders, plates, flanges, rings, blocks, bulbs, cover plates, reflectors, reflector carriers, mirror substrate blanks, lenses, carrier racks, bells, crucibles, protective shields, reactors and apparatus.

The physical and chemical properties of the material are influenced by undesired impurities and intentionally added dopants. Such impurities and dopants in addition to the main material are also referred to in the following as "ingredients". Ingredients in quartz glass are for example hydroxyl groups (OH), chlorine (Cl), fluorine (F) and metallic elements (Ge, B, P, Al, Ti, Fe etc.). Hydroxyl groups, for example, produce an absorption band in the infrared range, but can also improve the radiation resistance of quartz glass to UV radiation. Doping quartz glass with titanium dioxide up to 8% by weight reduces the coefficient of thermal expansion.

A particularly important property of such bodies made of glassy material is their refractive index and their spatial distribution. For example, the radial refractive-index profile of a fiber preform determines the waveguide properties of the optical fiber drawn from it. Many ingredients have an effect on the refractive index. Fluorine is a dopant that reduces the refractive index of quartz glass.

For the characterization of glass materials and particularly for the determination of the concentration of an ingredient in bodies of ceramic or glassy material, spectroscopic methods are frequently used, such as infrared or Raman spectroscopy. Absorption or scattering of electromagnetic measurement waves in or on a measurement sample is here evaluated. Raman measurements, for example, require high adjusting efforts. A particular drawback is, however, that measurement samples of a specific size have normally to be taken from the body of ceramic or glassy material and prepared under great efforts.

A non-destructive measurement method using sonic or ultrasonic waves avoids this drawback. The determination of the concentration of the ingredients is here based on an evaluation of the superposition of such sonic waves penetrating the body of ceramic or glassy material at least in part with other sonic waves that do not penetrate the body of ceramic or glass material or penetrate it along a shorter route. Such a measurement method is described in the technical article by Wei, Ting-Cun "*Acoustic properties of silica glass doped with flourine*", Journal of Non-Crystalline Solids 321 (2003), pp. 126-133.

Quartz glass samples with different fluorine concentrations are here analyzed by way of ultrasonic measurements (LSAW; leaky surface acoustic wave), illustrating that the propagation speed of the ultrasonic waves in the quartz glass body is linearly decreasing with an increasing fluorine concentration. Therefore, the measurement or calculation of the propagation speed of the ultrasonic waves in the quartz glass body allows the determination of the fluorine concentration. The propagation speed of the ultrasonic waves is determined by interference of pulsed tone burst signals without and with sound propagation through the measurement sample. Water is used as a coupling medium to couple the ultrasonic waves from the ultrasonic transducer into the measurement body.

US 2017/031006 A1 describes an optical method for detecting damage, material changes or contamination to a turbine blade and other metal or ceramic components. For this purpose, the phase and/or amplitude change of a reflected measuring beam compared to a reference beam unaffected by the workpiece is evaluated by means of "vector network analysis." The frequency range of the measuring beam is in the radio frequency, HF frequency or microwave frequency range.

In principle, also large-volume bodies of ceramic or glassy material can be non-destructively measured in each ultrasonic measurement. However, the in-coupling of the ultrasonic waves requires a complicated coupling technique or at least a coupling medium, for instance a water bath surrounding the glass or ceramic body. This prevents a measurement during the production process or at any rate makes it more difficult.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
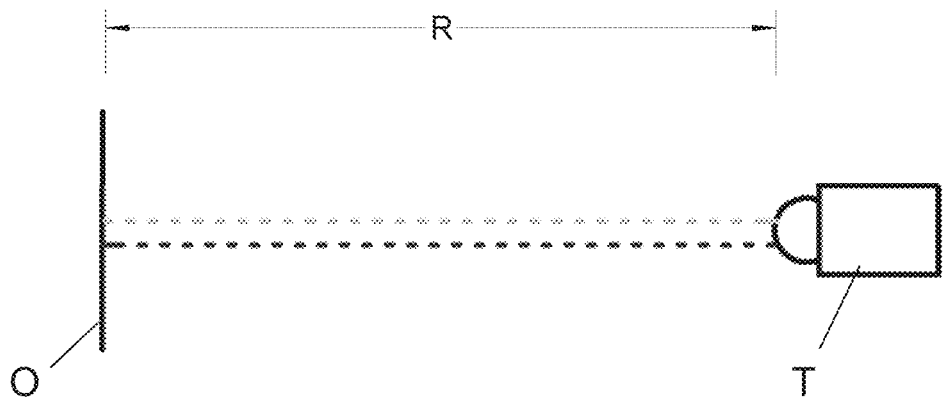
FIG. 1 illustrates a sketch for determining a distance between a transceiver for gigahertz radiation and a reflector.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

One embodiment indicates a non-destructive method for determining a concentration of an ingredient in a body of ceramic or glassy material that is also suited for a measurement in the production process of the corresponding body.

Based on the mentioned method, this is achieved according to one embodiment by using modulated gigahertz radiation, which covers the frequency range between 20 and 300 gigahertz, as the measurement wave.

The gigahertz radiation in the sense of one embodiment covers the frequency range between 20 and 300 gigahertz (GHz). This radiation is able to penetrate a body made of ceramic or glassy material independently of its chemical nature and its internal structure, such as porosity, density and color, without changing the material properties. However, the radiation itself undergoes a change in the glass, which can be determined as the change in propagation time of a measurement beam compared to the reference beam unaffected by the material. The change in propagation time results, for example, from the fact that the material has a magneto-optical, electro-optical, thermo-optical, or chemo-optical property, through which the incident gigahertz radiation can be changed and manifests itself as a change in propagation time. It has been illustrated that the change in propagation time depends in particular on the chemical composition of the material, so that the concentration of each constituent can be determined with an otherwise constant structure and composition of the material.

In the method according to one embodiment, the propagation time difference of measurement waves is thus determined, similar to ultrasonic wave measurements, but in contrast to this, a coupling medium can be dispensed with. This enables non-destructive measurement of the body made of ceramic or glassy material even during its manufacturing process.

The use of modulated gigahertz radiation reduces the effort required for sample preparation and eliminates the need for sampling. Thus, the measuring and evaluation effort is low compared to the spectroscopic analysis methods mentioned above.

The method according to one embodiment therefore combines the evaluation of propagation time differences from the known ultrasonic measurement, but does not use sound waves, but electromagnetic radiation, as in spectroscopic analysis methods. It therefore avoids the respective disadvantages of the known methods, especially with regard to sample preparation and the necessity of using coupling media.

The method according to one embodiment involves one or more transmitters for the emission of the gigahertz radiation, which usually passes through a beam optics by means of which the gigahertz radiation is directed onto the body made of ceramic or glassy material. The gigahertz radiation is reflected by the body made of ceramic or glassy material and/or by a reflector arranged opposite the transmitter in the radiation direction, and the reflected radiation is received by at least one receiver. Instead of measuring reflected radiation, a transmitter-receiver pair can also be located opposite each other on the body to be measured, which is made of ceramic or glassy material, so that the gigahertz radiation transmitted from the body is measured directly.

The propagation times can be measured by using radiation pulses that can be "localized" in time, or by imposing a time stamp on continuous wave radiation (CW radiation) by modulation. The time of the measurement signal received in the receiver is transmitted to an evaluation device, which determines the propagation time. The propagation time of gigahertz radiation passing through the body to be measured, which is made of ceramic or glassy material, is compared with the propagation time of radiation not passing through the body. The change in propagation time thus determined, caused by the material of the body made of ceramic or glassy material, is a measure of the concentration of the ingredient. A comparison of the propagation times thus illustrated the concentration of the ingredient. The modulation applies markings to the CW radiation to determine the propagation time.

The gigahertz radiation that does not pass through the body can be, for example, radiation that is reflected on the body, or gigahertz radiation in whose beam path the body made of ceramic or glassy material is not positioned, or gigahertz radiation whose propagation velocity is known, so that the propagation time can be determined from the knowledge about the length of the free path and the filling medium (for example, air) alone, even without renewed measurement.

In this method variant, the distance between transmitter and opposite receiver or between transmitter and receiver unit and reflector is known, so that the known propagation velocity of the gigahertz radiation (in air) can be used to determine the change in the propagation velocity caused by the material of the body made of ceramic or glassy material.

Transmitter and receiver can be combined in one component and can be arranged practically at the same location so that they always have the same distance from the body made of ceramic or glassy material, which simplifies the propagation time measurement. Such a component is called a "transceiver".

The case of unaffected back reflection of electromagnetic radiation on a reflecting object with the transmitter and receiver (transceiver) in the same position is illustrates schematically in FIG. 1. The electromagnetic radiation emitted by the transmitter unit of the transceiver T passes through the free air path to the reflecting object O twice until it is detected again by the receiver unit of the transceiver T. The following general relationship then applies between the propagation time t and the distance R to the reflecting object O:

$$R = c_0 \times t/2 \qquad (1)$$

With: R=distance between transceiver and reflector
$c_0$=light speed in air [m/s]
t=propagation time [s]

Figure 2:
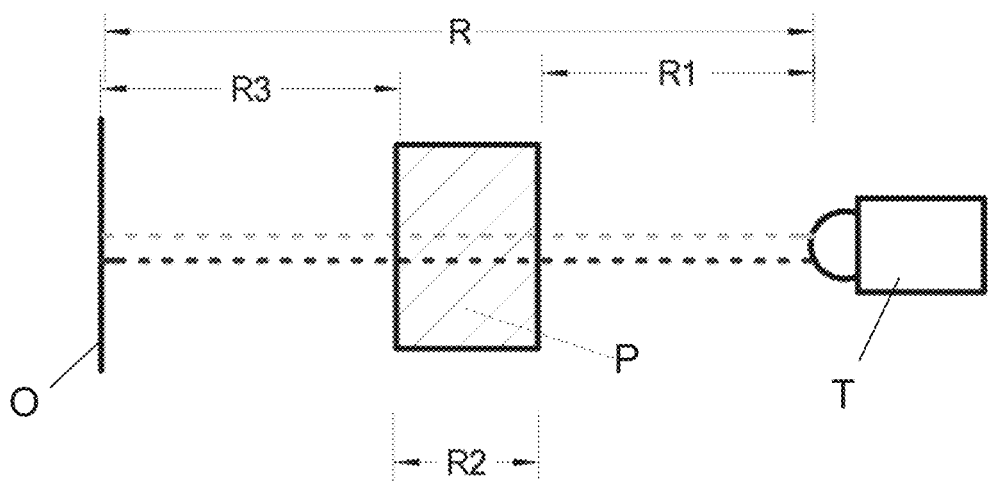
FIG. 2 illustrates the sketch of FIG. 1 with a measurement sample in the optical path of the electromagnetic radiation.

FIG. 2 schematically illustrates the case where there is a sample P in the beam path, which sample changes the propagation velocity of the electromagnetic radiation. Compared to the propagation time t used in equation (1), there is a change in the propagation time $|\Delta t_p|$ from which the propagation velocity $c_p$ of the electromagnetic radiation in the sample can be calculated according to equation (2).

$$c_p = R2/(R2/c_0 + \Delta t_p) \qquad (2)$$

With R1, R3=paths in air
R2=sample measurement
$c_p$=radiation propagation velocity in the sample
$|\Delta t_p|$=propagation time change The propagation velocity $c_p$ is a measure for the material of the sample and in particular for its material constants, which depend on the chemical composition and density.

The radiation optics, for example, includes one or more lenses which focus the gigahertz radiation emitted by the at least one transmitter onto a central axis of the body to be measured, which is made of ceramic or glassy material. In this way, bodies made of ceramic or glassy material with different lateral dimensions can be measured without the need for tracking of the measuring device or the radiation optics.

Alternatively, the radiation optics can also include a collimator, wherein the gigahertz radiation emitted by the transmitter is guided as a parallel beam through the body made of ceramic or glassy material. This has the advantage that position changes of the body of ceramic or glassy material perpendicular to the beam direction have little influence on the measurement result.

The method according to one embodiment can be used for measuring a body made of a glass with a high silicic acid content, for example, of quartz glass, wherein the ingredient includes, for example, hydroxyl groups, hydrogen, a metal oxide and/or a halogen, and wherein the ingredient is in one embodiment fluorine.

For example, the quartz glass body may also be present as a so-called "soot body" made of porous, lightly compressed $SiO_2$ soot, which is a semi-finished product for the production of preforms for optical fibers or other products made of high-purity synthetic quartz glass. Also bodies made of ceramic or glassy material, which absorb visible light or infrared radiation, can be measured by means of the method according to one embodiment, since the gigahertz radiation is able to penetrate such bodies in a layer thickness sufficiently large for the measurement.

This applies equally to opaque, porous glass, for example, opaque quartz glass, as well as to titanium-containing glass, which is used for the production of mirror substrate blanks with a low coefficient of thermal expansion.

The modulation of the gigahertz radiation is performed, for example, by modulating the phase and/or the amplitude and/or the frequency and/or the effective wavelength and/or the wave front. However, in one embodiment, the gigahertz radiation is periodically frequency modulated; for example and in one embodiment frequency-modulated continuous wave radar is used, so-called FMCW radiation.

The periodic frequency modulation can include one frequency burst or several frequency bursts. A given frequency range can be traversed once or several times.

The body made of ceramic or glassy material is in one embodiment penetrated by the gigahertz radiation from different measurement directions, a respective optical path length or a respective signal propagation time being determined for each measurement direction.

The body made of ceramic or glassy material is penetrated by one or more transmitters in different directions with the gigahertz radiation which is received by one or more receivers and converted into electrical signals, wherein the propagation times of the gigahertz radiation are measured and wherein a spatial distribution of the concentration of the ingredient is obtained from the propagation times of the gigahertz radiation.

Transmitters and receivers can, for example, be arranged opposite each other. Several transmitters and receivers can also be arranged in pairs around the circumference of the body made of ceramic or glassy material. Each pair of transmitter and receiver can be designed as a transceiver, wherein several transceivers are distributed around the circumference of the body to be measured, which is made of ceramic or glassy material.

The body made of ceramic or glassy material can be rotated along its central axis relative to the receiver-transmitter pair. In one embodiment method variant, however, the body made of ceramic or glassy material is positioned stationary with respect to at least one transmitter for the gigahertz radiation, the transmitter being moved around the body made of ceramic or glassy material in order to determine a three-dimensional profile of the ingredient concentration.

In one embodiment, however, at least one pair of a receiver and a transmitter is rotated around the longitudinal axis or a virtual central axis of the body made of ceramic or glassy material during a measurement process. The pair of transmitter and receiver can in turn be a transceiver. By rotating around the ceramic or glassy body to be measured, several pairs of transmitters and receivers can be simulated. In this way, the concentration of the ingredient can be determined with spatial resolution.

The movement of the transmitter around a virtual central axis around the body made of ceramic or glassy material is usually followed by the radiation optics. The reflector can be designed in such a way that it completely surrounds the body made of ceramic or glassy material, so that in this case a movement of the reflector around the axis of rotation is not required.

In order to avoid multiple reflections that can interfere with the measurement result, the distance between the surface of the body made of ceramic or glassy material and the transmitter or receiver is in one embodiment greater or smaller than the dimension of the body situated in the main emission direction of the gigahertz radiation.

The method according to one embodiment serves to determine the concentration of an ingredient in a body of ceramic or glassy material, for example, a cylindrical optical object, such as a preform for optical fibers of quartz glass.

Figure 3:
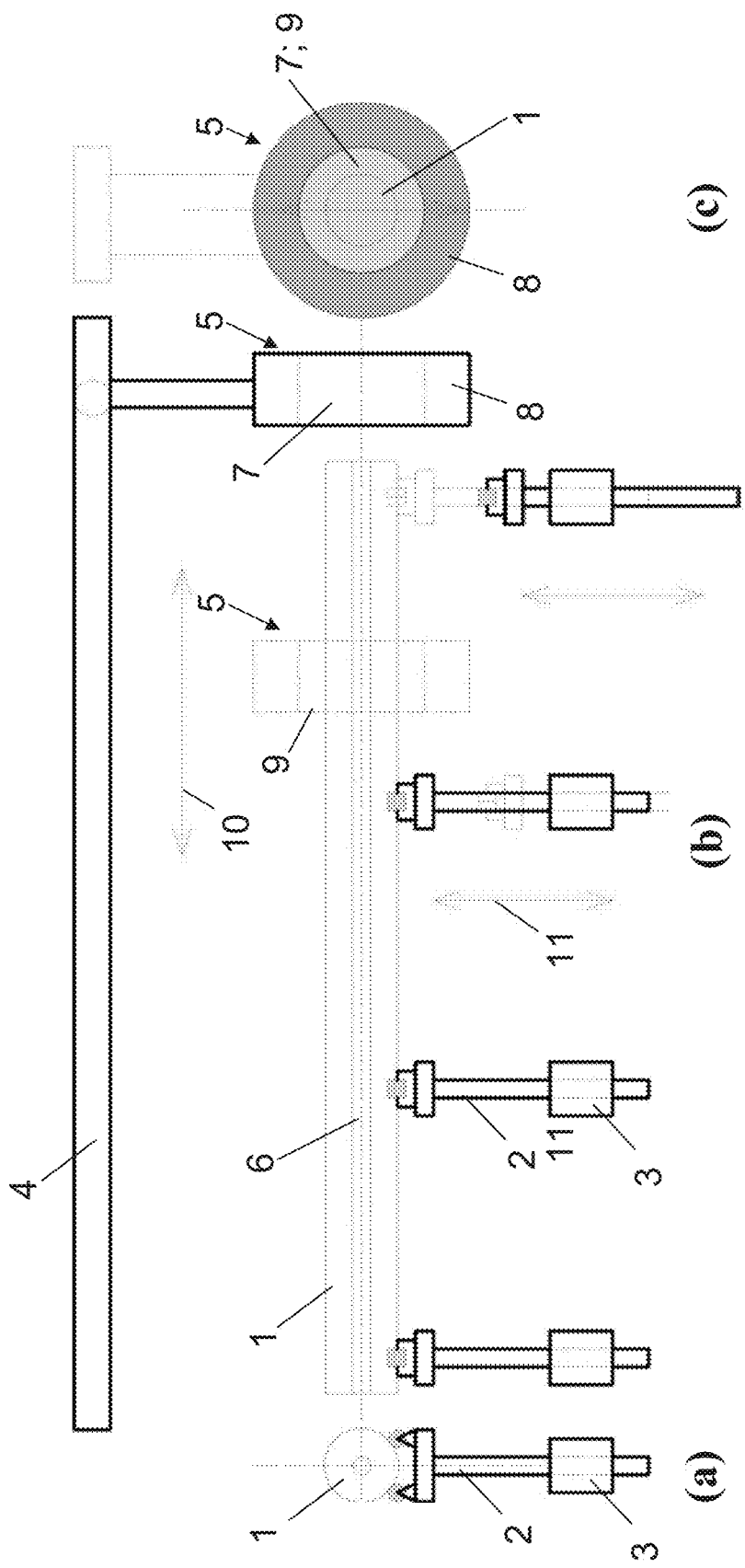
FIG. 3 illustrates a device for the spatial measurement of a cylindrical body with continuous wave radar radiation in a schematic illustration, wherein (b) is a longitudinal view, (a) is a front view and (c) is a rear view.

FIG. 3 schematically illustrates an embodiment of a device suitable for carrying out the method according to one embodiment. The body of ceramic or glassy material is in the form of a hollow cylinder 1 of quartz glass. It rests on several sample supports 2 distributed evenly over the length, each of which is equipped with lifting and lowering devices 3 by means of which the sample support 2 can be moved vertically upwards into a supporting position and downwards into a release position, as indicated by the direction arrows 11.

Above the hollow cylinder 1 there is a linear guide 4 for a commercially available radar measuring device 5, which is designed as an annular component. The circular ring 8 surrounds a central opening 7 which is larger than the outer diameter of the hollow cylinder 1. The radar measuring device 5 is mounted on the linear guide 4 in such a way that the central axis of the central opening 7 and the longitudinal axis 6 of the hollow cylinder 1 are coaxial with each other. Therefore, the radar measuring device 5 can be moved along the longitudinal axis 6 of the hollow cylinder 1 by means of the linear guide 4.

The radar unit 5 includes a transmitter for emitting frequency-modulated radar radiation with a frequency of 80 GHz and a receiver for this radiation, which are combined in the form of a transceiver. The transceiver can be moved within the circular ring 8 around the central axis along a circular path together with a radiation optic, as indicated by direction arrow 10. The radiation optic serves to focus the radar beam on the central axis and thus also on the longitudinal axis 6 of the hollow cylinder. The width of the annular gap 9 between the transceiver (circular ring 8) and the outer shell of the hollow cylinder 1 is known. The transmitter and the receiver are connected to an evaluation and control device (not illustrated).

To determine the fluorine concentration in the quartz glass of the hollow cylinder 1 to be measured, the propagation times of the radar radiation are determined by means of the radar device 5. The propagation speed of the radar radiation emitted by the transmitter is delayed differently depending on the material constants of the quartz glass, which have an influence on the refractive index.

In order to exclude the influence of other material constants which would interfere with the fluorine concentration measurement, a calibration measurement is carried out on a standard quartz glass body where the fluorine concentration is known and which otherwise does not differ from the quartz glass of the hollow cylinder 1 to be measured.

The propagation velocity determined using the standard body (or the propagation time of the radar waves) can be easily compared with the corresponding propagation time measurement using the hollow cylinder 1 to be measured and, if necessary, with a propagation time measurement without a radiation-penetrated sample.

The outer diameter of the hollow cylinder 1 is determined with an accuracy with a standard deviation of less than 10 μm and entered into the evaluation and control device. In the embodiment, the outer diameter averaged over the length is 201.60 mm, and the width of the annular gap 9 is 24.2 mm.

The wall thickness of the hollow cylinder 1 can be determined by means of generally known tactile or optical measuring methods. However, an elegant measuring method is the one in which the wall thickness (R2) of the hollow cylinder is determined using the same radar measuring technique by evaluating the reflections, which are reflected back by a reflector onto the receiver, of the radar radiation of inner wall of the cylinder and outer wall of the cylinder (with and without sample). From the measured data transmitted by the transceiver and the known wall thickness of the hollow cylinder, the evaluation and control device determines the propagation speed of the radar waves, or the difference between the propagation speeds with and without hollow cylinder 1 in the beam path. Due to the difference in propagation time, the material constants of the quartz glass of the hollow cylinder 1 can be inferred.

For example, in the case of hollow cylinders 1 made of quartz glass with unknown but different fluorine concentrations, the concentration of this dopant can be determined on the basis of the above equations (1) and (2), provided that all other material constants influencing the propagation speed of the radar waves are unchanged.

By rotating the radar source 5 around the longitudinal axis 6, a mean refractive index for different azimuthal directions (angles) is obtained, that is, on the whole an azimuthal profile of the propagation velocity at each axial position of the radar source 5, which can be converted into an azimuthal refractive-index profile at the measuring wavelength.

Figure 4:
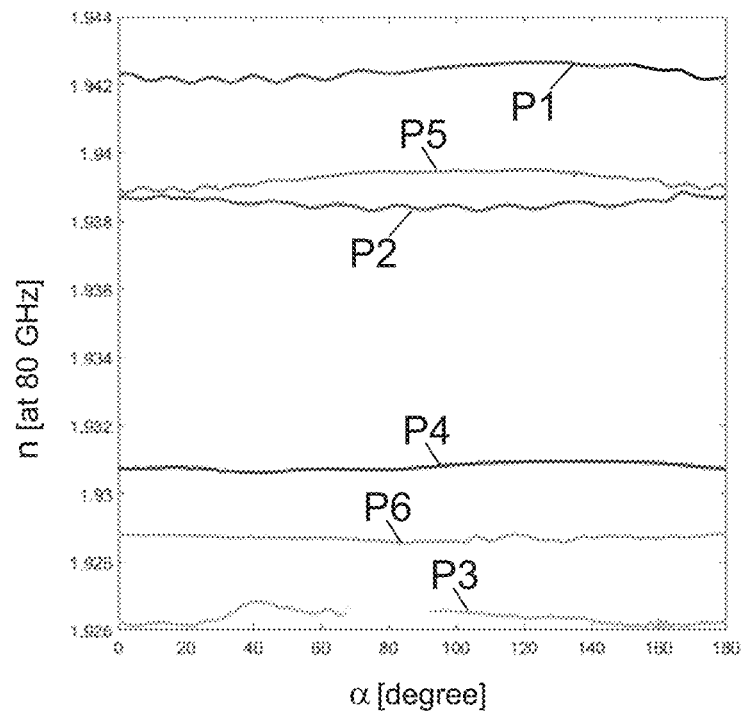
FIG. 4 illustrates a diagram with refractive index profiles in the case of electromagnetic radiation of a frequency of 80 GHz, which profiles have been determined by measurement of a cylindrical quartz glass body with continuous wave radar radiation.

The diagram in FIG. 4 illustrates azimuthal refractive-index profiles determined in this way, which have thereby been determined on six hollow cylinders 1 of quartz glass with different fluorine doping (the images are taken from about the middle of each hollow cylinder). The refractive index n is plotted against the angle of incidence a (in angular degrees) on the ordinate. Accordingly, all hollow cylinders P1 to P6 illustrate an approximately uniform azimuthal refractive-index profile at different levels. In column 3 of Table 1, the respective refractive-index mean values are given.

Figure 5:
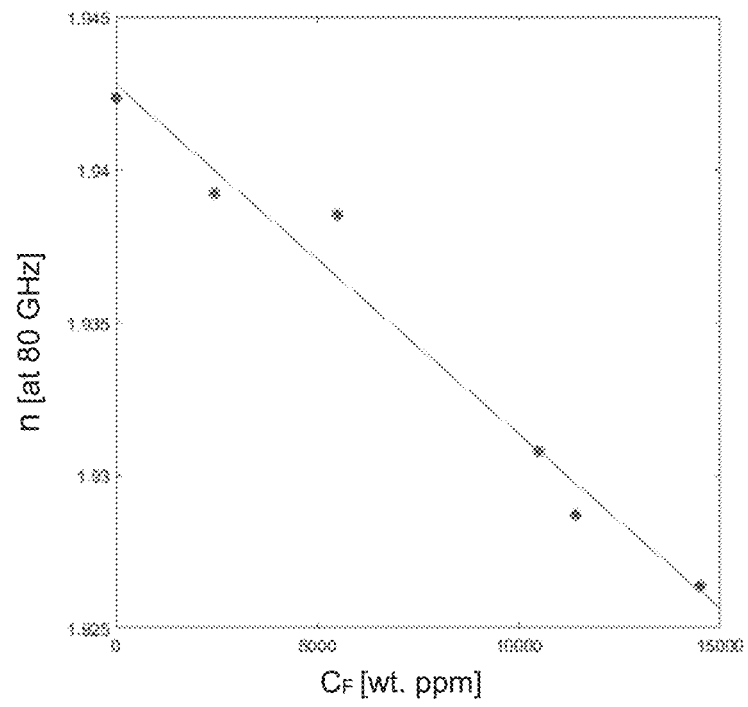
FIG. 5 illustrates a diagram which illustrates the fluorine concentration averaged over the wall thickness of a hollow cylinder in a quartz glass body as a function of a mean refractive index at an electromagnetic radiation of a frequency of 80 GHz.

The fluorine concentrations CF of samples P1 to P6 were determined on the basis of the analysis method described above using ultrasonic waves. In the diagram of FIG. 5, the mean values of the refractive index n are plotted against the fluorine concentrations CF (in ppm by weight). This illustrates that there is an approximately linear relationship between the fluorine concentrations CF and the refractive index. Column 2 of Table 1 lists the respective measured fluorine concentrations CF. Thus, a specific fluorine concentration can be assigned to each refractive-index mean value on the basis of a simple calibration measurement.

TABLE 1

| Sample | $C_F$ [wt. ppm] | n (at 80 GHz) |
|---|---|---|
| P1 | 0 | 1.9523 |
| P2 | 5,500 | 1.9485 |
| P3 | 14,500 | 1.9415 |
| P4 | 10,500 | 1.9445 |
| P5 | 2,440 | 1.9511 |
| P6 | 11,420 | 1.9438 |

By translating the radar source 5 along the longitudinal axis 6 of the hollow cylinder in the direction of the direction arrow 10, an axial profile of the fluorine concentration in the hollow cylinder 1 is obtained. The sample supports 2 are controlled in such a way that they are moved from the support position to the release position as soon as the radar source 5 passes their position.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. A method of determining the concentration of an ingredient in a body of ceramic or glassy material, comprising:
measuring one of the optical path length and the signal propagation time of a measurement wave penetrating the glass body in a measurement direction, characterized in that modulated gigahertz radiation that covers the frequency range between 20 to 300 gigahertz is used as the measurement wave.

2. The method according to claim 1, characterized in that the body comprises a glass with a high silicic acid content, and that the ingredient comprises at least one of hydroxyl groups, hydrogen, a metal oxide and a halogen.

3. The method according to claim 2, characterized in that the body comprises quartz glass.

4. The method according to claim 2, characterized in that the ingredient is fluorine.

5. The method according to claim 1, characterized in that the gigahertz radiation is frequency-modulated.

6. The method according to claim 1, characterized in that the glass body is penetrated by the gigahertz radiation from different measurement directions, wherein a respective optical path length or a respective signal propagation time is determined for each measurement direction.

7. The method according to claim 1, characterized in that the body of ceramic or glassy material is positioned in a stationary manner in relation to at least one transmitter for the gigahertz radiation, wherein the transmitter is moved for the determination of a three-dimensional profile of the ingredient concentration around the body of ceramic or glassy material.

8. The method according to 1, characterized in that the distance between the surface of the body of ceramic or glassy material and a transmitter or receiver is greater than the dimension of the body situated in the main emission direction of the gigahertz radiation.

9. The method according to 1, characterized in that the distance between the surface of the body of ceramic or glassy material and a transmitter or receiver is smaller than the dimension of the body situated in the main emission direction of the gigahertz radiation.

10. The method according to claim 2, characterized in that the gigahertz radiation is frequency-modulated.

11. The method according to claim 4, characterized in that the gigahertz radiation is frequency-modulated.

12. The method according to claim 2, characterized in that the glass body is penetrated by the gigahertz radiation from different measurement directions, wherein a respective optical path length or a respective signal propagation time is determined for each measurement direction.

13. The method according to claim 4, characterized in that the glass body is penetrated by the gigahertz radiation from different measurement directions, wherein a respective optical path length or a respective signal propagation time is determined for each measurement direction.

14. The method according to claim 2, characterized in that the body of ceramic or glassy material is positioned in a stationary manner in relation to at least one transmitter for the gigahertz radiation, wherein the transmitter is moved for the determination of a three-dimensional profile of the ingredient concentration around the body of ceramic or glassy material.

15. The method according to claim 4, characterized in that the body of ceramic or glassy material is positioned in a stationary manner in relation to at least one transmitter for the gigahertz radiation, wherein the transmitter is moved for the determination of a three-dimensional profile of the ingredient concentration around the body of ceramic or glassy material.

* * * * *